(12) United States Patent  
Keilen (10) Patent No.: US 8,491,582 B2  
(45) Date of Patent: Jul. 23, 2013

(54) BONE COMPRESSION AND DISTRACTION SYSTEM

(75) Inventor: Adam John Keilen, Kalamazoo, MI (US)

(73) Assignee: Lithos Surgical Innovations, LLC, Kalamazoo, MI (US)

(*) Notice: Subject to any disclaimer, the term of this patent is extended or adjusted under 35 U.S.C. 154(b) by 257 days.

(21) Appl. No.: 13/072,549

(22) Filed: Mar. 25, 2011

(65) Prior Publication Data

US 2011/0172662 A1  Jul. 14, 2011

Related U.S. Application Data

(63) Continuation-in-part of application No. 12/905,310, filed on Oct. 15, 2010, now abandoned.

(60) Provisional application No. 61/279,049, filed on Oct. 15, 2009.

(51) Int. Cl.  
*A61B 17/66* (2006.01)

(52) U.S. Cl.  
USPC .......................................................... 606/57

(58) Field of Classification Search  
CPC ...................................................... A61B 17/66

USPC .................. 606/57–59, 90, 105; 403/43–48; 411/389, 390  
See application file for complete search history.

(56) References Cited

U.S. PATENT DOCUMENTS

| 4,988,349 | A  | * | 1/1991 | Pennig | 606/58 |
| 5,330,474 | A  | * | 7/1994 | Lin | 606/267 |
| 8,057,473 | B2 | * | 11/2011 | Orsak et al. | 606/57 |

* cited by examiner

*Primary Examiner* — Eduardo C Robert  
*Assistant Examiner* — David Comstock  
(74) *Attorney, Agent, or Firm* — Endurance Law Group PLC (57) ABSTRACT

A bone compression and distraction system which has an apparatus and a plurality of pins. The apparatus includes a body, a worm screw and a pair of pin attachment members. The worm screw is placed in the body and the pin attachment members are coupled to the worm screw, and constrained from rotation relative to the worm screw, wherein the worm screw has opposing threads extending away from a central region. Upon rotation of the worm screw, the pin attachment members travel in opposite directions, either toward each other or away from each other to either decrease or increase the spacing therebetween. A pin may be coupled to each of the pin attachment members.

21 Claims, 8 Drawing Sheets

BONE COMPRESSION AND DISTRACTION SYSTEM

CROSS-REFERENCE TO RELATED APPLICATION

This application is a continuation in part of U.S. patent application Ser. No. 12/905,310 filed Oct. 15, 2010 now abandoned, entitled Bone Compression and Distraction Apparatus, which claims priority from U.S. Prov. Pat. App. Ser. No. 61/279,049 filed Oct. 15, 2009, entitled Bone Compression and Distraction Apparatus, the entire disclosure of each is hereby incorporated by reference.

BACKGROUND OF THE DISCLOSURE

1. Field of the Disclosure

The present disclosure is directed toward the field of bone compression and distraction medical instruments and more particularly to a bone compression and distraction system having an apparatus and pin member. The apparatus includes opposing worm gears that provide for micro-adjustable linear compression and distraction as well as improved ease of use.

2. Background Art

The use of bone compression and distraction instruments are well known in the art. Typically, a bone compression and distraction instrument has a dome line working plane versus the line compression and distraction as discussed in the present disclosure. Prior art utilizes a scissor action, pinned joints, or a rack and pinion drive. These methods are not as effective and require more applied force, more personnel involvement, and obstruct the surgical field view.

Problematically, many bone compression and distraction instruments are excessively large, which preclude their use for smaller joints, maxillofacial, podiatric, or hand surgeries. However, there are some smaller bone compression and distraction instruments, but they are often composed of complex assemblies and require a large number of parts which can prove quite costly. Additionally, many bone compression and distraction instruments are hard to clean and sterilize.

It is an object of the present disclosure to provide a bone compression and distraction apparatus with micro-adjustable linear compression and distraction, manually, with a ratchet or the like, or utilizing other devices.

It is another object of the present disclosure to provide a bone compression and distraction apparatus of a small size which allows for the successful use of the apparatus for procedures on the smallest joints.

It is another object of the present disclosure to provide a bone compression and distraction apparatus with fewer parts, easier assembly and improved cleaning over previous instruments.

These objects as well as other objects of the present disclosure will become apparent in light of the present specification, claims, and drawings.

SUMMARY OF THE DISCLOSURE

The disclosure, in one aspect thereof, is directed to a bone compression and distraction apparatus comprising a body, a worm screw, a first pin attachment member and a second pin attachment member. The body includes an elongated tubular member which defines a cavity having a first end and a second end. An assembly slot extends along the length of the elongated tubular member between the first end and the second end. The worm screw extends through the body within the cavity and is spaced apart from the body. The worm screw has a first end, a second end and a central region. A right hand thread extends from the central region toward the first end. A left hand thread extends from the central region toward the second end. The worm screw is configured to rotate about a longitudinal axis extending therethrough while being precluded from translating within the cavity of the body.

The first pin attachment member is threaded onto the worm screw on the side having the right hand thread and has an arm extending through the assembly slot in the body with the arm having a pin coupling member. The second pin attachment member is spaced apart from the first pin attachment member and threaded onto the worm screw on the side having the left hand thread. The second pin attachment member has an arm extending through the assembly slot in the body with the arm having a pin coupling member.

Upon rotation, the worm screw causes the first pin attachment member and the second pin attachment member to move in opposing directions along the assembly slot of the body (i.e., toward or away from each other).

In a preferred embodiment, the assembly slot defines the outer range of movement of the first pin attachment member and the second pin attachment member.

In another such preferred embodiment, the assembly slot extends from one end of the body to the other end of the body stopping short of either edge.

In another preferred embodiment, the assembly slot comprises a linear channel extending along the body that allows the first pin attachment member and the second pin attachment member to move along the assembly slot in opposing directions.

In another preferred embodiment, a plurality of access slots are positioned along the body providing access to the cavity to aid in sterilization.

In another preferred embodiment, the cavity has a substantially uniform cross-section.

In some such preferred embodiments, the first pin attachment member and the second pin attachment member each include a body that is circular in configuration, which slidably engages the cavity.

In a preferred embodiment, a closed end cap is positioned on one end of the body and an open end cap is positioned over the ratchet end of the worm screw. These structures allow the worm screw to rotate about a longitudinal axis when activated by turning the ratchet end.

In another preferred embodiment, the coupling member of the first pin attachment member and the coupling member of the second pin attachment member each comprise a plurality of through holes. The through holes are each of a predetermined diameter and are configured to allow a pin to pass therethrough so that it can be anchored to a bone.

In another preferred embodiment, the body has a plurality of indicia marking distances along the assembly slot.

In a preferred embodiment, the pin coupling member of the first and second pin attachment member further includes an elongated tube depending therefrom, with a hole that is extending therethrough.

In another preferred embodiment, the elongated tube extends at least one of perpendicular and oblique to the arm as the arm extends through the assembly slot.

In a preferred embodiment, the hole terminates within the elongated tube, thereby defining a blind hole.

In a preferred embodiment, the elongated tube is rotatable relative to the arm, allowing for rotation of the arm, and in turn the body while being in use.

In another aspect of the disclosure, the disclosure is directed to a system which includes the above-described bone compression and distraction apparatus in combination with at least two pins. Each pin includes a first end and a second end. Each pin has a pointed sharp tip on the first end, and a blunt end on the second end.

In one such embodiment, the pin has a stop to limit movement thereof relative to the pin coupling member.

In another aspect of the disclosure, the disclosure is directed to a pin for use with a bone compression and distraction apparatus. The pin includes a pin body and a standard pin coupling interface. The pin body includes a first end, a second end with a sharp tip on the first end, and a blunt end on the second end. The interface is positioned between the first and second end. The interface includes an outwardly conical portion terminating with a cylindrical portion. These are configured to interface with a bone distraction and compression apparatus thereby allowing the pin to come in various different diameters while having a standard connection with the apparatus.

Additionally, the apparatus and system of the present disclosure is made from fewer parts than many prior art devices, which can have a positive impact on costs. Additionally, due to the construction, the bone compression and distraction apparatus of the present invention can be made smaller than conventional devices and can be utilized in procedures performed on smaller joints. There is a plurality of access slots and an assembly slot along the body of the bone compression and distraction apparatus, which helps the process of cleaning and sterilizing. It is contemplated that the apparatus is provided in a plastic box to hold the components when not in use. The box has openings on its outer surface, which allows the disclosure to be cleaned and sterilized when stored within the box.

BRIEF DESCRIPTION OF THE DRAWINGS

The disclosure will now be described with reference to the drawings wherein.

DETAILED DESCRIPTION OF THE DISCLOSURE

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 1:
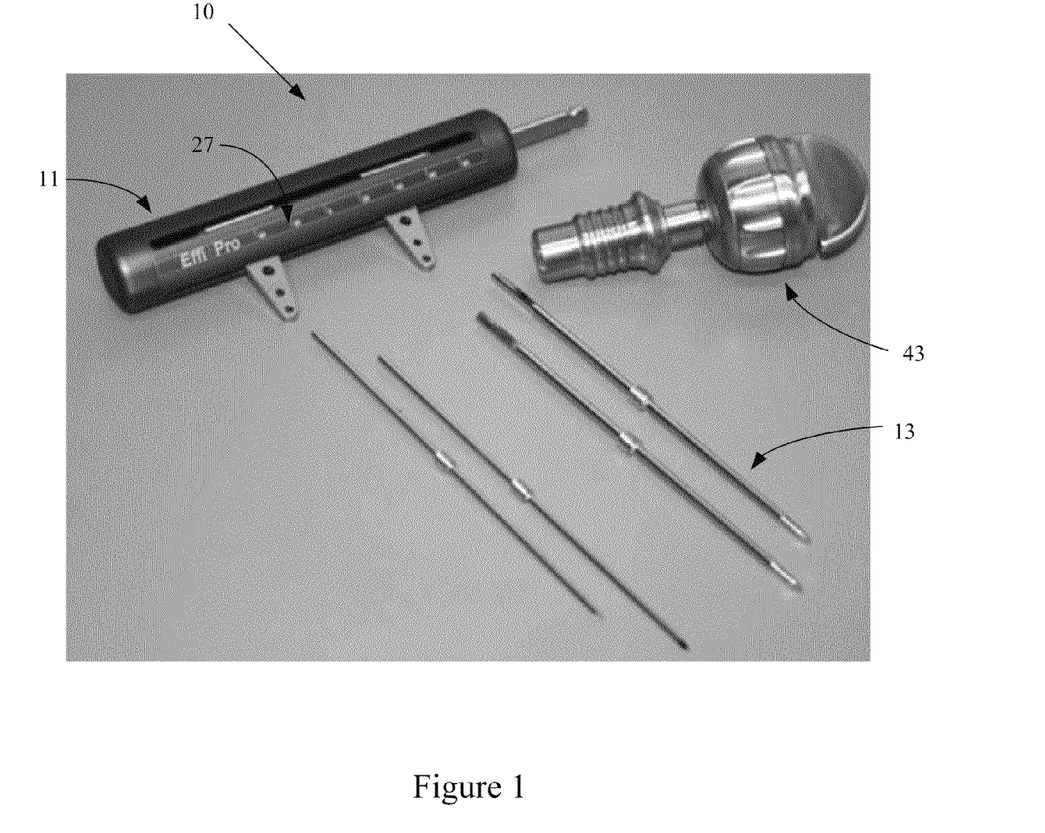
FIG. 1 of the drawings is a perspective view of the bone compression and distraction system of the present disclosure.

Bone compression and distraction system 10 is shown in FIG. 1 as comprising bone compression and distraction apparatus 11 and a plurality of pins, such as pin 13. A ratchet 43 may also be provided to manipulate the apparatus. The system comprises a light-weight apparatus that provides both compression and distraction in one product and in one manual function. The system also provides improved visibility at the surgical site. The bone compression and distraction system has various surgical indications, such as, but not limited to, arthroscopy, spine procedures, grafting etc. Additionally, it will be understood that the system provides micro-adjustable compression and distraction.

Preferably, the bone compression and distraction apparatus 11 has all metal components designed for cleaning and sterilizing. The bone compression and distraction apparatus 11 is generally provided in a plastic box that holds the components when they are not in use. The plastic box includes openings on its outer surface, which allows the bone compression and distraction apparatus to be sterilized while it is within the plastic box. The bone compression and distraction apparatus 11 is, it is contemplated, intended to have several years of service life. In other embodiments, it is contemplated that certain components may be provided in polymer form to provide a disposable or recyclable device. Additionally, it will be understood that the device can be used for external fixation but that it is not limited thereto, and could be implantable in certain embodiments.

Figure 2:
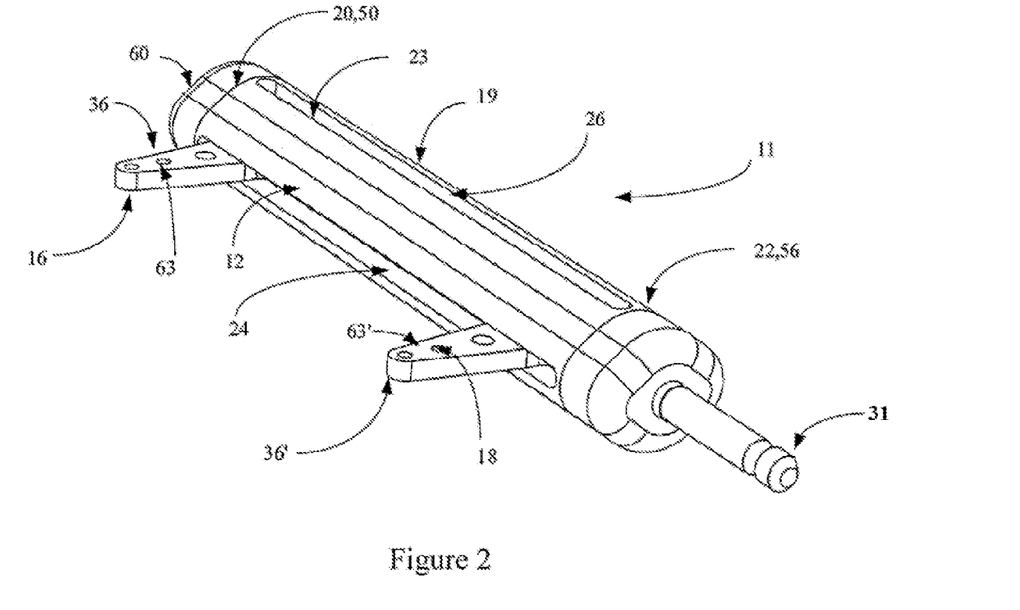
FIG. 2 of the drawings is a perspective view of the bone compression and distraction system of the present disclosure.
Figure 3:
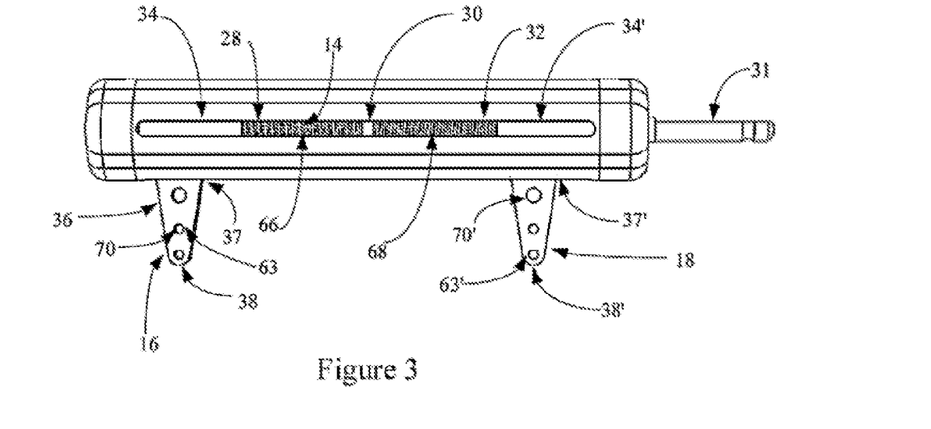
FIG. 3 of the drawings is a top plan view of the bone compression and distraction apparatus of the present disclosure.

With reference to FIGS. 2 and 3, the bone compression and distraction apparatus 11 comprises a body assembly 12, a worm screw 14, a first pin attachment member 16, and a second pin attachment member 18. The bone compression and distraction apparatus 11 may be formed from a number of different metal members, most preferably, such as, for example, an anodized aluminum for the body assembly 12 and stainless steel for the first pin attachment member 16 and the second pin attachment member 18. A disposable version is contemplated for use, wherein some of the components comprise plastic components for reduction of weight and cost. Of course, the apparatus is not limited to construction from any particular metal or any particular material.

The body assembly 12 includes elongated body 19, open end cap 54 and closed end cap 60. The elongated body 19 comprises an elongated tubular member that is somewhat elliptical or oval-like shaped (hereinafter oval-like shape) which defines a cavity 23 which is suitable for grasping and retaining by a user, such as a doctor or surgeon. The elongated body 19 includes a first end 20, a second end 22, an assembly slot 24, and a plurality of additional slots, such as access slot 26. The first end 20 has an opening 50 with an oval-like cross-sectional configuration. The cross-sectional configuration of the body is substantially uniform across the length thereof. As a result, the second end 22 includes opening 56 which has a cross-sectional configuration identical to that of opening 50.

The elongated body 19 has the assembly slot 24 disposed on the surface thereof. The assembly slot 24 extends between the first end 20 and the second end 22 stopping short of the actual edge. In other configurations, the slot extends across the entirety of the elongated body. However, in the present configuration, added structural integrity is exhibited by not slicing the slot all the way across the elongated body and stopping short of the edge. As will be explained, the apparatus is constructed so that the first pin attachment member 16 and the second pin attachment member 18 can be inserted into the slot when at least one of the open end cap 54 and the closed end cap 56 are separated from the elongated body 19.

It is contemplated that the different slots, such as access slots 26, are located on different surfaces of the body. It will be understood that the body contemplated includes four separate surfaces or flatter regions of the oval-like shape, and different slots are disposed along these different slots. These cleaning slots allow for cleaning fluid to easily enter into the cavity 23 to assist with cleaning. It will be understood that while the cleaning slots 26 are shown as elongated slot members, other types of openings are likewise contemplated of various shapes, including elongated slots, circular openings, and other arbitrary and non-arbitrary configurations.

It is contemplated that the body is approximately 4" in length, although it is contemplated that the body may be shorter or longer, depending on the particular use. It is also contemplated that a number of different sized apparatuses may be provided, each allowing for a differently sized set of pin attachment members and wherein the pin attachment members have a different range of motion. In other embodiments a single apparatus may be provided of different length. Additionally, indicia 27 may be placed along the assembly slot 24 so that the user can determine the distance between the right and second pin attachment members. This indicia may be laser etched into the surface, or may be otherwise applied to the surface.

The open end cap 54 extends over the first end 20 of the elongated body 12 so as to seal the opening 50 thereof, and prevent ingress thereinto. Preferably, the open end cap is constructed from an anodized aluminum alloy and, as will be described below, the inside of the open end cap includes a housing (not shown) and bushing (not shown) which is configured for receipt of the end of the worm gear. The open end cap may be coupled to the elongated body 19 by way of an adhesive, a press fit, or other mechanical entrapment (i.e., the use of pins, rivets or fasteners and the like). Openings may be provided in the open end cap 54 so as to facilitate cleaning if needed.

The closed end cap 60 extends over the second end 22 so as to seal the opening 56 thereof. The closed end cap includes an opening 57 which allows for the worm screw 14 to extend therethrough and terminate at a ratchet end 31. As with the open end cap 54, the closed end cap 60 prevents ingress into the cavity 23. Preferably, the closed end cap is constructed from an anodized aluminum alloy, and, as will be described below, the housing includes a housing with a bushing which receives the worm gear so as to allow relative rotation of the worm screw about the body assembly 12.

The worm screw 14, as shown in FIGS. 2 and 3, includes a first end 28, a central region 30, and a second end 32. A right hand thread 66 extends from the central region 30 toward the first end 28. A left hand thread 68 extends from the central region 30 toward the second end 32. It will be understood that the threads may be reversed, as long as either side has opposing threads. The particular pitch of the threads can be varied to achieve the correct, desired linear movement per rotation and to have the threads exert a predetermined force based upon rotation force applied (so as to provide the desired mechanical advantage).

At least one end of the worm screw 14 extends beyond the first end 20 of the elongated body 19 and the second end defines a ratchet end 31 upon which ratchet 43 (FIG. 1) can be attached. In other embodiments, a manual grasping member (such as a butterfly head) can be permanently or removably coupled to the ratchet end 31. Generally, the user manipulates the worm screw 14 through the ratchet end 31.

The worm screw 14 interfaces with the body 12, and in particular the closed end cap 60 at one end and the open end cap 54 at the other end, so as to rotatably be positionable within the cavity 23 along its own longitudinal axis while not being able to translate therewithin. Through suitable bushings, or bearing surfaces, the worm screw is retained by each of the end caps. The configuration that is preferred is that the worm screw is centrally located within the elongated body 19 so as to be spaced apart from any one of the walls. As will be understood, additional bracing may be positioned within the body 12 to retain the worm screw and to keep the worm screw from translating within the elongated body.

Typically, the worm screw 14 is constructed from a stainless steel member, although other types of materials are contemplated, including but not limited to other typically bio compatible materials (Titanium/Aluminum alloys, Cobalt/Chromium alloys, among others).

The first pin attachment member 16 comprises a body member 34, arm 36 and pin coupling member 63. The body member 34 includes a bore which is threaded so as to matingly engage the threads of the worm screw (and in particular that of the right hand thread). Generally, the body member 34 is configured to fit within the elongated slot 19 and to be slidable therewithin. Preferably, the body member occupies much of the cross-sectional configuration of the cavity 23 while being spaced therefrom so as to not interfere or otherwise bind along the cavity 23 and the elongated body 19.

The arm 36 extends from the body member 34. The arm 36 is configured to extend through the assembly slot 24 when the body member 34 is positioned in the desired configuration. The arm 36 comprises a substantially planar member, includes proximal end 37 and distal end 38, although a number of different structures are likewise contemplated. Generally, it is integrally formed with the body member 34 so as to be a monolithic structure. In other embodiments, the body member 34 may be a separate member from the arm 36 and the two may be welded together, or attached through an interference fit, or otherwise adhered or fastened together.

The pin coupling member 63 may comprise a number of different structures. With reference to FIG. 2, the pin coupling member 63 comprises a plurality of openings, such as openings 70, which extend through the arm 36. Preferably, the different openings extend through the arm perpendicular to the planar surface such that when inserted, the pins 96 are substantially perpendicular to the arm. In the embodiment disclosed, a plurality of openings are provided so as to be capable of receiving a number of differently sized pins and to additionally provide a plurality of locations wherein the pin can be coupled to the arm. Further, the multiple openings also provide for multiple pins to be coupled to an arm at any given time.

Figure 4:
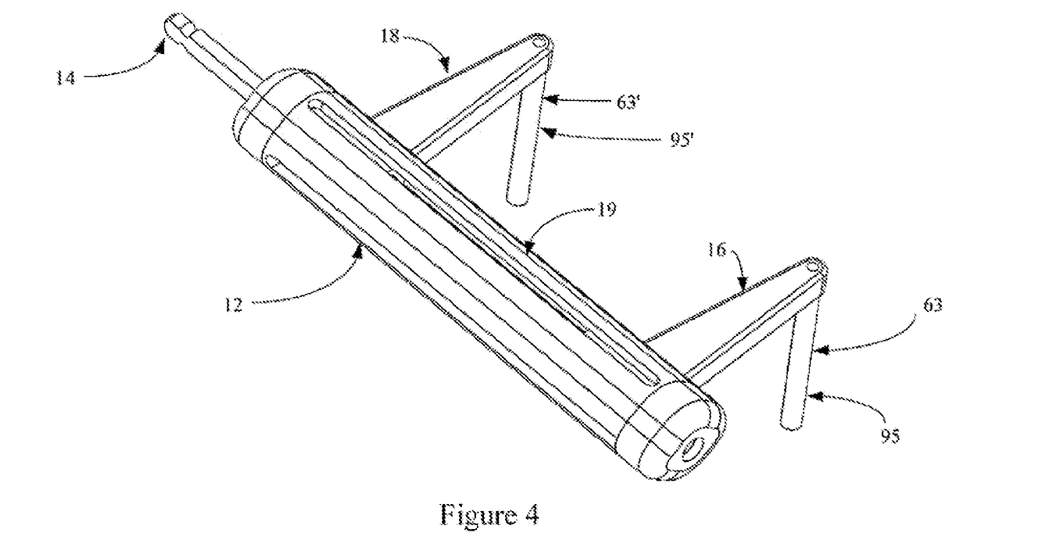
FIG. 4 of the drawings is a perspective view of the bone compression and distraction apparatus of the present disclosure, showing the elongated tubes installed with through holes.
Figure 6A:
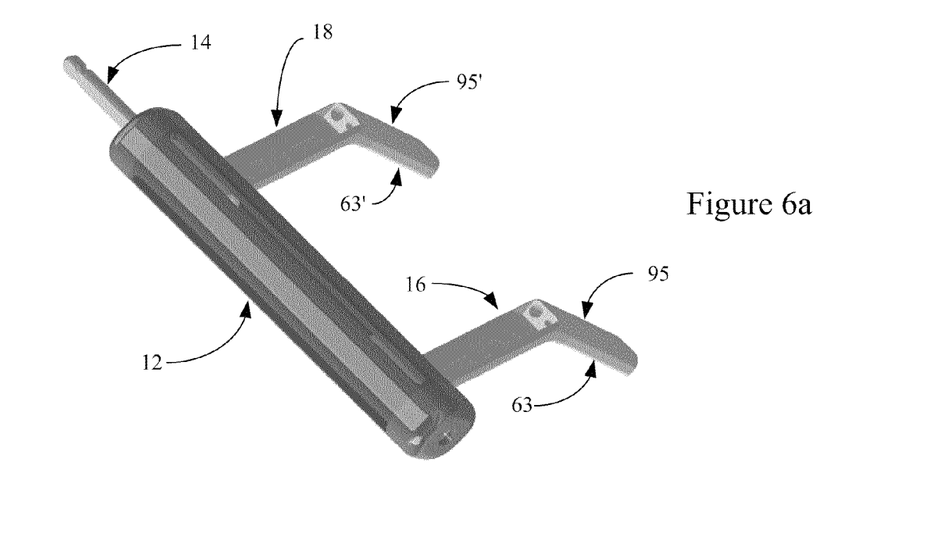
FIG. 6a of the drawings is a perspective view of the bone compression and distraction system of the present disclosure, showing the oblique elongated tubes of the apparatus having pins within the through holes.
Figure 6B:
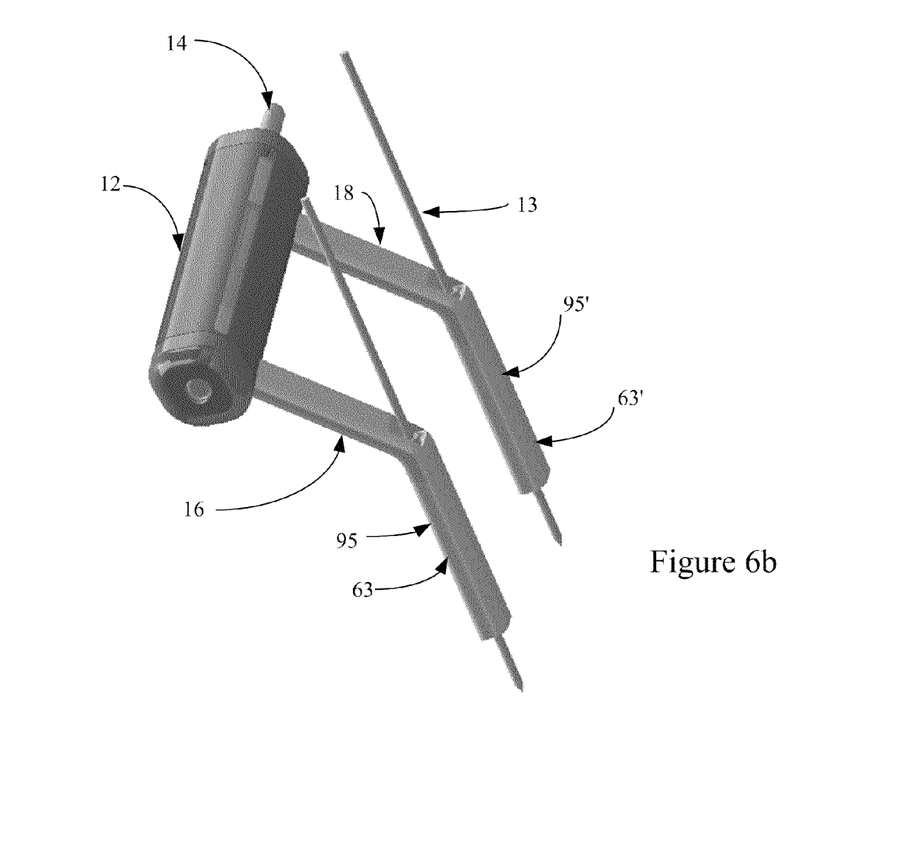
FIG. 6b of the drawings is a perspective view of the bone compression and distraction system of the present disclosure, showing the oblique elongated tubes of the apparatus having pins within the through holes, and showing the pins inserted into the elongated tubes.

In another embodiment, with reference to FIG. 4, the pin coupling member 63 may comprise an elongated tube, such as elongated tube 95 which is coupled to the respective arm 36 and which extends therefrom. The tube 95 cooperates with openings, such as opening 70 to provide an elongated channel which can support the respective pin member and which can provide additional rigidity to the overall apparatus. In the embodiment of FIGS. 6a and 6b, the elongated tube 95 can be integrally formed with the respective arm 36 and can extend in oblique to the arm.

Figure 5:
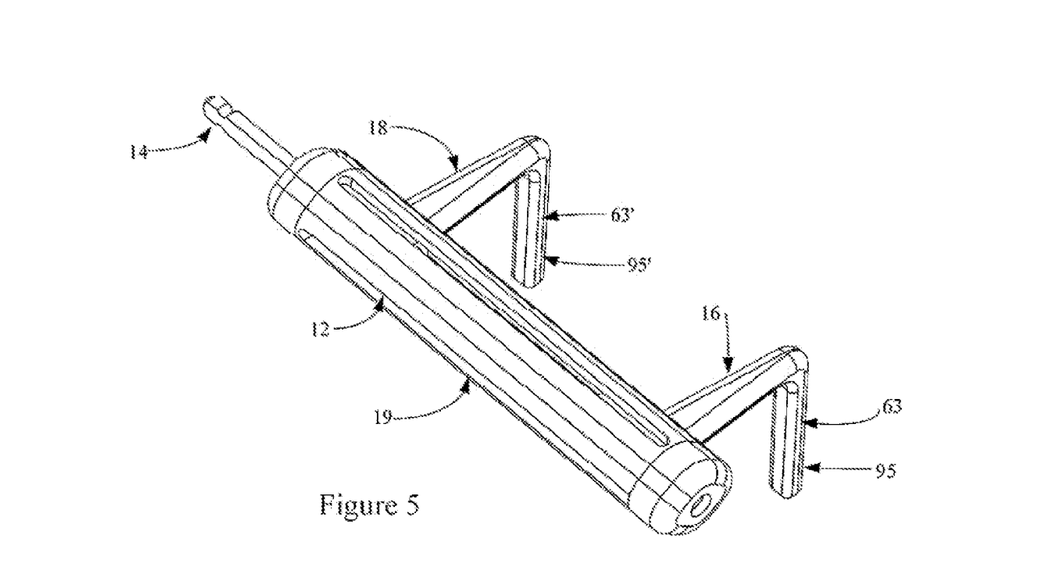
FIG. 5 of the drawings is a perspective view of the bone compression and distraction apparatus of the present disclosure, showing integrated elongated tubes installed with blind holes.
Figure 7A:
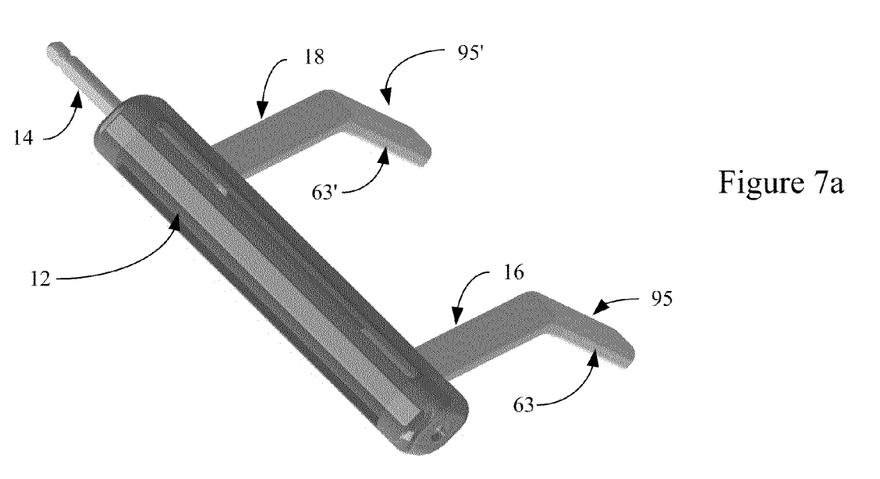
FIG. 7a of the drawings is a perspective view of the bone compression and distraction system of the present disclosure, showing the oblique elongated tubes having the blind holes.
Figure 7B:
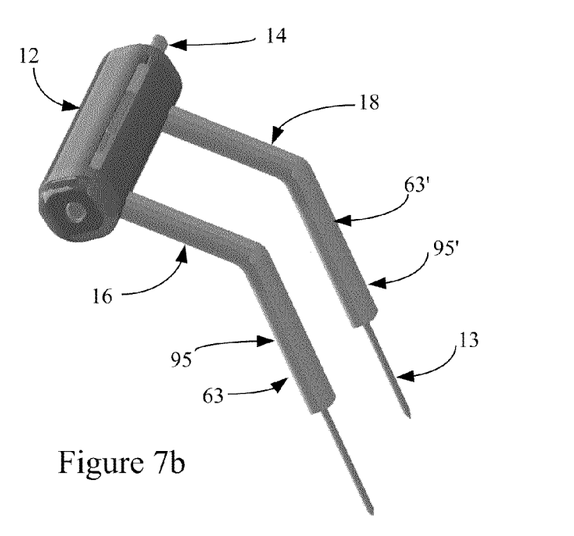
FIG. 7b of the drawings is a perspective view of the bone compression and distraction system of the present disclosure, showing the oblique elongated tubes having the blind holes, and showing the pins inserted into the elongated tubes.
Figure 8:
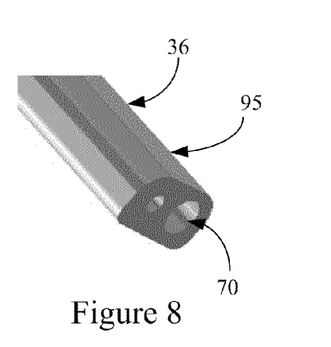
FIG. 8 of the drawings is a perspective view of the elongated tubes showing the holes extending thereinto (of course, other embodiments may have fewer or greater numbers of holes)

In other embodiments, such as the embodiment shown in FIG. 5, the tube 95 of the pin coupling member 63 may be coupled to the respective arm and the tube can terminate thereat. In such a configuration, the tube 95 defines a blind opening which has a termination point. Thus, the pin can be inserted thereinto. In the embodiment shown in FIGS. 7a and 7b, the tube 95 may retain the blind opening, but be disposed oblique to the respective arm 36. In such an embodiment, multiple holes can be provided for different pin sizes (FIG. 8).

Figure 9A:
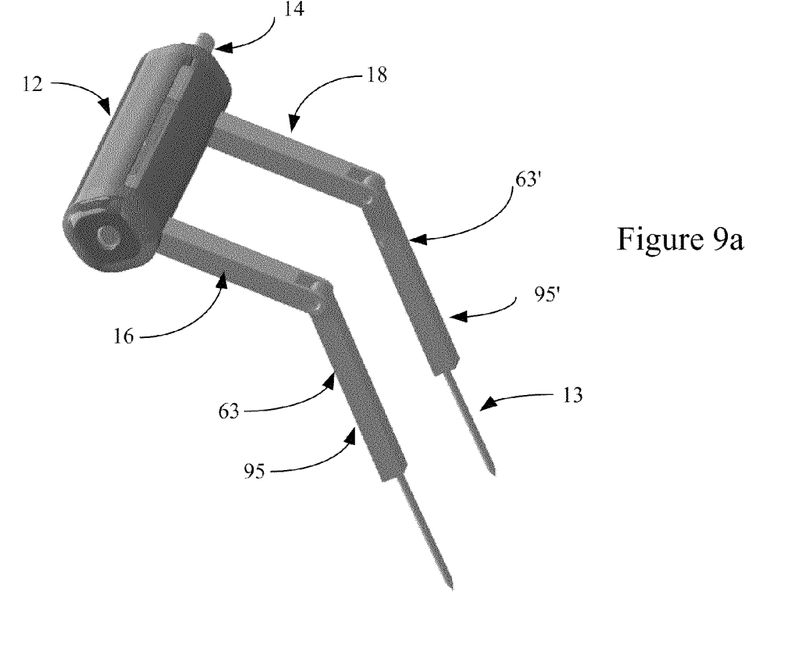
FIG. 9a of the drawings is a perspective view of the bone compression and distraction system of the present disclosure, showing the elongated tubes which are rotatably coupled to the respective arms, and which include blind holes.
Figure 9B:
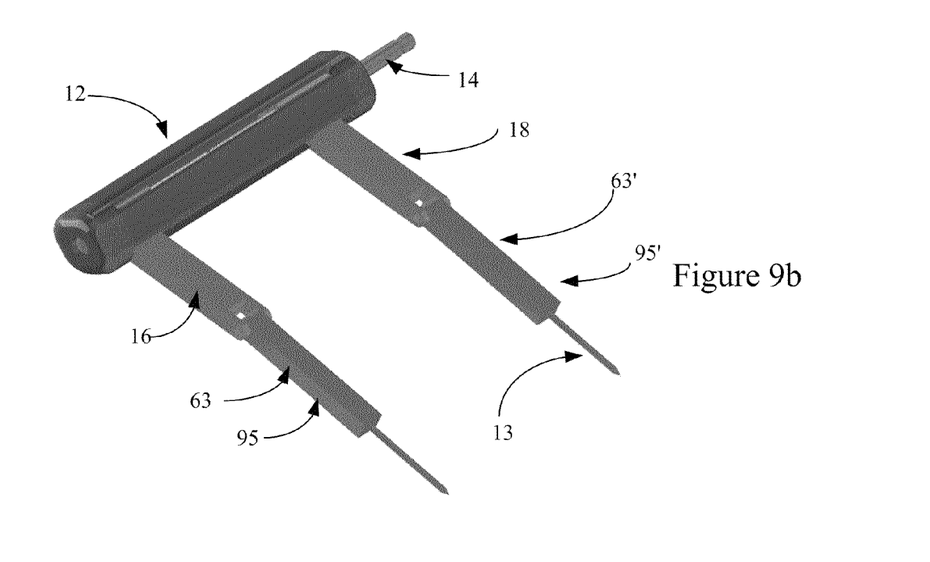
FIG. 9b of the drawings is a perspective view of the bone compression and distraction system of the present disclosure, showing the elongated tubes which are rotatably coupled to the respective arms, and which include blind holes, and showing the pins inserted into the elongated tubes.

It will be understood that in another embodiment, as is shown in FIGS. 9a and 9b, the elongated tube can be rotatably positionable relative to the respective leg. As such, the angle can be modified as necessary. It will be understood that a locking screw or other mechanism can be utilized to achieve locking of the components relative to each other.

Referring again to FIGS. 2 and 4, the second pin attachment member 18 is a substantially identical mirror image of the first pin attachment member, although the two pin attachment members may have different configurations. As such, like structures have been identified with the same reference numeral, augmented with a (') prime. More specifically, the second pin attachment member comprises body member 34', arm 36' and pin coupling member 63'. The body member 34' includes a bore which is threaded so as to matingly engage the threads of the worm screw (and in particular that of the left hand thread). Generally, the body member 34' is configured to fit within the elongated slot 19 and to be slidable therewithin. Preferably, the body member occupies much of the cross-sectional configuration of the cavity 23 while being spaced therefrom so as to not interfere or otherwise bind along the cavity 23 and the elongated body 19.

The arm 36' extends from the body member 34'. The arm 36' is configured to extend through the assembly slot 24 when the body member 34' is positioned in the desired configuration. The arm 36' comprises a substantially planar member having proximal end 37' distal end 38', although a number of different structures are likewise contemplated. Generally, it is integrally formed with the body member 34' so as to be a monolithic structure. In other embodiments, the body member 34' may be a separate member from the arm 36 and the two may be welded together, or attached through an interference fit, or otherwise adhered or fastened together.

The pin coupling members 63' may comprise a number of different structures. With reference to FIG. 2, the pin coupling member 63' comprises a plurality of openings, such as openings 70' which extend through the arm 36'. Preferably, the different openings extend through the arm perpendicular to the planar surface such that when inserted, the pins 96 are substantially perpendicular to the arm. In the embodiment disclosed, a plurality of openings are provided so as to be capable of receiving a number of differently sized pins and to additionally provide a plurality of locations wherein the pin can be coupled to the arm. Further, the multiple openings also provide for multiple pins to be coupled to an arm at any given time.

It will be understood that the tube 95 and 95' in the various embodiments of FIGS. 3 through 9b are generally identical mirror images of each other. It will be understood, however, that either one of the tubes may be different than the other of the tubes, and various combinations are contemplated. Additionally, it will be understood that while configurations of tubes perpendicular to the arm or orthogonal to the arm at approximately 45° are merely optional configurations, and other angular displacements are likewise contemplated, such as angles between 0° and 90°. It will also be understood that if the tubes are parallel to the respective arm, they will likely be blind openings.

Figure 10:
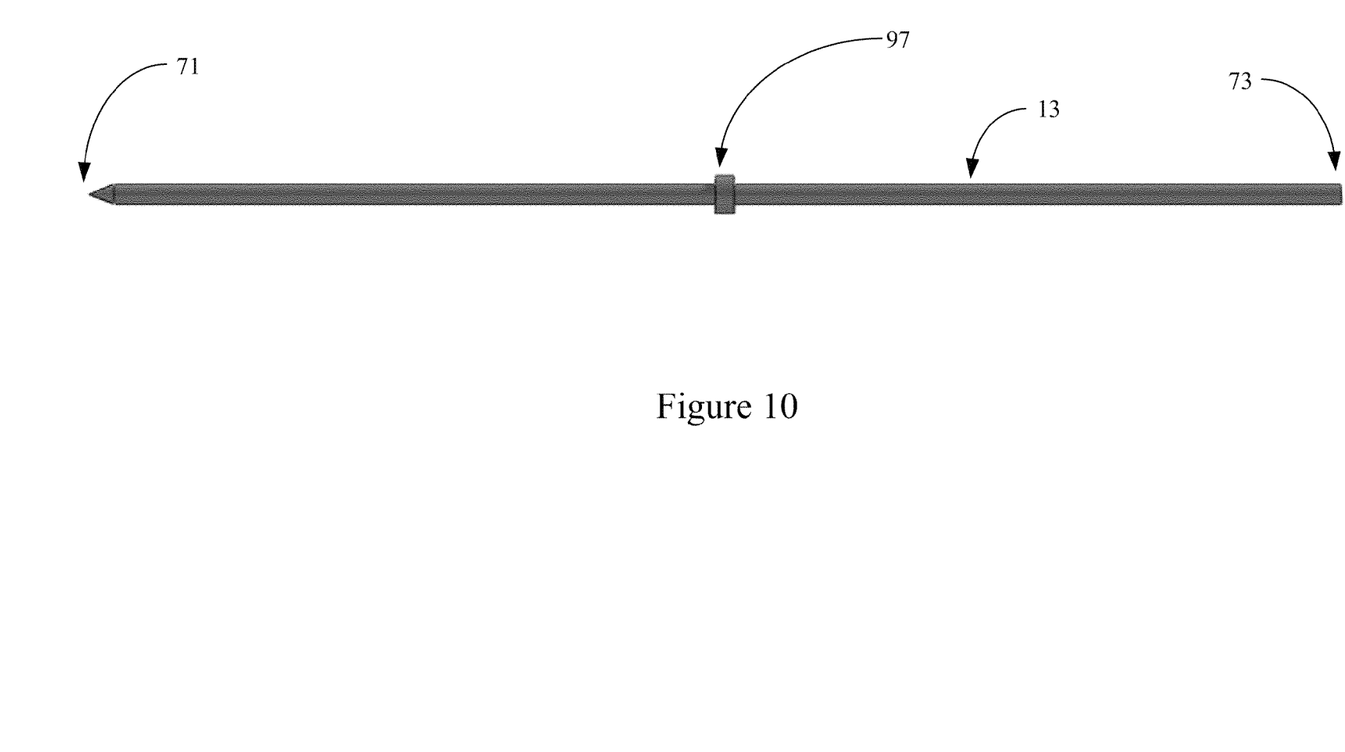
FIG. 10 of the drawings is a top plan view of the pin having a stop in the center of the pin.

With reference to FIGS. 1 and 10, the apparatus is configured for use in a system, which includes a plurality of pins, such as pin 13. The pins 13 have a pointed sharp tip on one end 71, and blunt end 73, having diameters ranging from 1.5 mm to 4 mm and lengths from 2 inches to 8 inches depending on the application. Of course, these dimensions are merely illustrative and are not to be deemed as being deemed limiting.

Additionally, as shown in FIG. 10, the pins 13 have a stop 97 to prevent potential slide off. The stops 97 can be made from wound wire stops, machined stops, a flat washer welded to a pin or a rubber or plastic washer or o-ring that is able to slide but held in place with friction etc. It will be understood that the pins 13 are not required to have the stop 97. The pins 13 can be threaded starting at the sharp tip and for the complete length of the pin if needed.

Figure 11A:
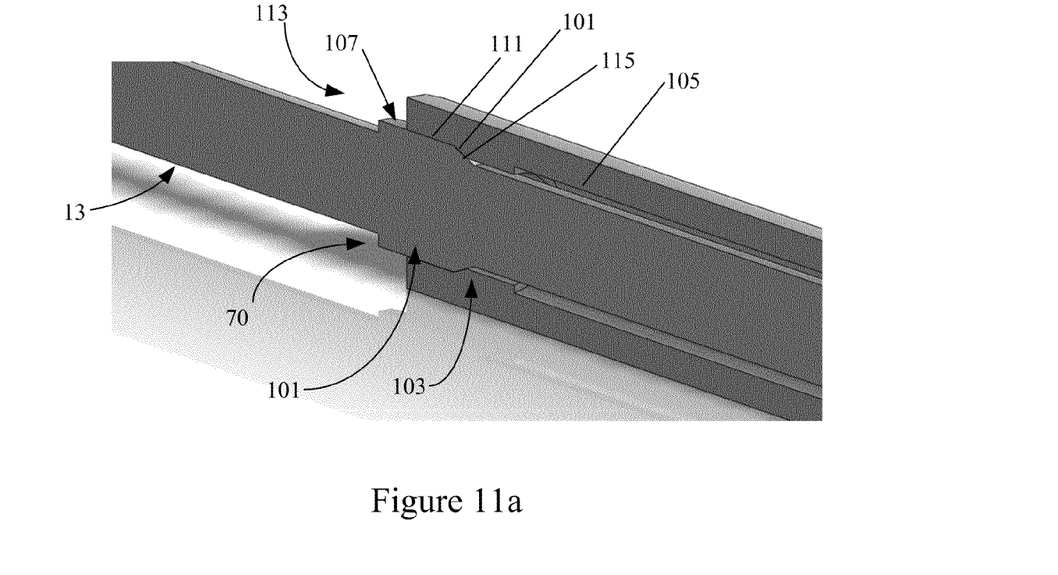
FIG. 11a of the drawings is a partial perspective view of the pin showing, in particular, the standard coupling interface in a first pin size.
Figure 11B:
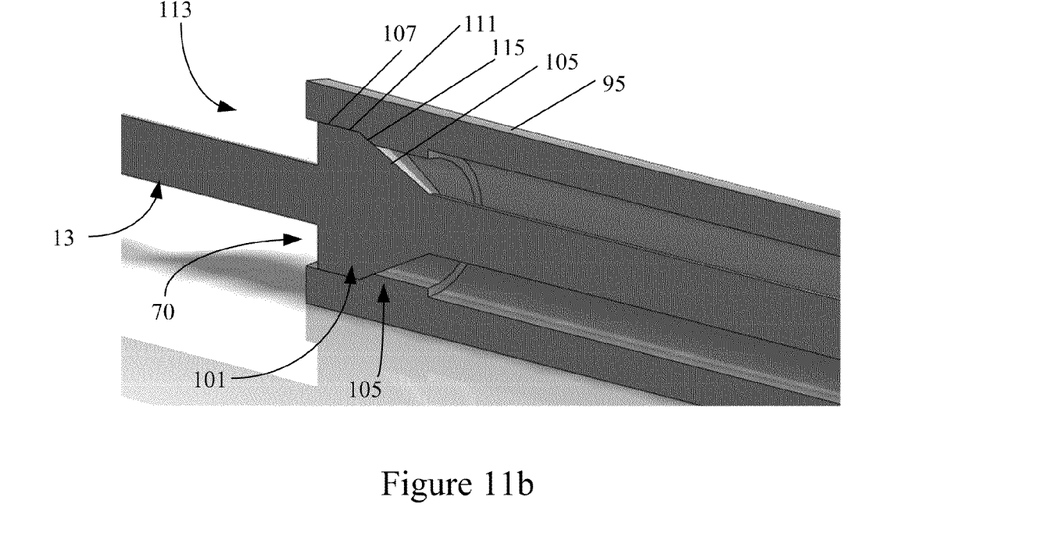
FIG. 11b of the drawings is a partial perspective view of the pin showing, in particular, the standard coupling interface in a second pin size.

Referring now to FIGS. 11a and 11b, while it is contemplated that the respective pin coupling members 63' include a sufficient amount of openings to fit any number of different diameter pins, it is likewise contemplated that the pins may include a standard coupling interface 113. The standard coupling interface includes pin coupling interface 101 which releasably couples to a standard arm coupling interface 103. In such an embodiment, the standard pin coupling interface includes an outwardly conical portion 105 which extends outwardly from the pin in the direction of the pointed end thereof, and a cylindrical portion 107 that extends from the conical portion 105. The cylindrical portion 107 has a diameter which is generally larger than the diameter of the underlying pin.

The standard arm coupling interface 103 includes a cylindrical bore 111 which terminates in a inwardly conical bore 113. The cylindrical bore is generally the same as the bore of the opening of the pin coupling member 63, whereas the inwardly conical bore is smaller. Each of the two bores are generally larger than the diameter of any one of the pins that may be inserted thereinto.

It will be understood that as the pin member 13 is inserted into the opening 70 of the pin coupling member 63, eventually, the pin coupling interface 101 makes contact with and extends into the opening. The cylindrical portion 107 of the pin coupling interface 101 interfaces with the cylindrical bore 111 and the conical portion 105 interfaces with the inwardly conical bore 113. As a result, the two structures interface closely and the conical bore precludes further movement of the pin member within the pin coupling member, thereby effectively locking the same in place.

Advantageously, in such a configuration, a single opening is capable of handling an plurality of differently sized pin members and it is not necessary to provide a plurality of openings 70. It will be understood that this can also allow for a more versatile apparatus while limiting the size thereof.

In operation, and with reference to FIG. 1, the user first obtains the system. Typically, the system can be stored on a tray with the apparatus and the requisite pins in a number of sizes. The tray may include a number of openings which can provide access to the tools for purposes of sanitizing the same. In other embodiments, a disposable version can be provided that is shipped in a sterilized pouch or other sterilized packaging. Of course, the manner of packaging is not to be deemed as limiting.

Once supplied, the user selects the pins which will be utilized. It will be understood that different surgical procedures will require differently sized pins. For example, smaller bones will require smaller pins as larger pins may be of a diameter which is too large to be secured into a particular bone or bone component.

Next, the user typically begins the procedure (after preparation utilizing x-rays or other images) by directing pins into bones that are to be compressed or distracted. The pins are spaced apart from each other and put in predetermined locations. The user then couples the pins to opposing pin attachment members.

Specifically, the respective pin is directed into the respective pin coupling member. Depending on the embodiment, the pin may be directed into an elongated opening, a blind opening or a through opening. The opening may be disposed obliquely or perpendicularly to the arms of the respective pin attachment members.

Once positioned and coupled, the pins can be moved relative to each other. To achieve movement of the pins (and in turn, compression or distraction of the bone), the user rotates the ratchet end 31 of the worm screw which either directs the pin attachment members toward or away from each other. This rotation is translated into simultaneous linear motion of the pins either toward or away from each other, thereby providing for linear distraction and compression. The user can utilize the indicia 27 on the elongated body to determine the precise movement of the worm screw.

In certain embodiments, the user can couple a device, such as a ratchet to the ratchet end 31 to assist with rotation of the worm screw. Indeed, the ratchet allows for rotation in a first direction, but precludes rotation in a second direction (and the directions can be swapped, typically, by means of a switch or lever). In other embodiments, the movement may be controlled by a separate controller device which could be powered and which would allow for very precise movements. In still other embodiments, a simple butterfly head can be utilized. The invention is not limited to any particular configuration of the ratchet end or means that assist the ratchet end. Due to the configuration of the worm screw, micro-adjustments are easily achieved by the user.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A bone compression and distraction apparatus comprising: A body having an elongated tubular member defining a cavity with a first end and a second end, wherein an assembly slot extends along the length thereof between the first end and the second end; A worm screw extending through the body within the cavity and spaced apart from the body having a first end, a second end, and a central region: a right hand thread extending from the central region toward the first end; a left hand thread extending from the central region toward the second end; at least one end of the worm screw extending beyond the first end of the body and terminating at a ratchet end; and the worm screw configured to rotate about a longitudinal axis extending therethrough while being precluded from translating within the cavity of the body; A first pin attachment member threaded onto the worm screw on the side having the right hand thread and having an arm extending through the assembly slot in the body with the arm having a pin coupling member; and A second pin attachment member spaced apart from the first pin attachment and threaded onto the worm screw on the side having the left hand thread and having an arm extending through the assembly slot in the body with the arm having a pin coupling member; Whereupon rotation of the worm screw causes the first pin attachment member and the second pin attachment member to move in opposing directions along the assembly slot of the body.

2. The bone compression and distraction apparatus of claim 1, wherein the assembly slot defines the outer range of movement of the first pin attachment member and the second pin attachment member.

3. The bone compression and distraction apparatus in claim 2, wherein the assembly slot extends from one end of the body to the other end of the body stopping short of either edge.

4. The bone compression and distraction apparatus in claim 3, wherein the assembly slot comprises a linear channel extending along the body that allows the first pin attachment member and the second pin attachment member to move along the assembly slot in opposing directions.

5. The bone compression and distraction apparatus in claim 1, wherein a plurality of access slots are positioned along the body providing access to the cavity to aid in sterilization.

6. The bone compression and distraction apparatus in claim 1, wherein the cavity has a substantially uniform cross-section.

7. The bone compression and distraction apparatus in claim 6, wherein the first pin attachment member and the second pin attachment member each include a body that is circular in configuration, which slidably engages the cavity.

8. The bone compression and distraction apparatus in claim 1, wherein a closed end cap is positioned on one end of the body and an open end cap is positioned over the ratchet end of the worm screw, which allows the worm screw to rotate about a longitudinal axis when activated by turning the ratchet end.

9. The bone compression and distraction apparatus in claim 1, wherein the coupling member of the first pin attachment member and the coupling member of the second pin attachment member each comprise: a plurality of through holes, each of a predetermined diameter, configured to allow a pin to pass therethrough to be anchored to a bone.

10. The bone compression and distraction apparatus in claim 1, wherein the body has a plurality of indicia marking distances along the assembly slot.

11. The bone compression and distraction apparatus of claim 1, wherein the pin coupling member of the first and second pin attachment member further includes an elongated tube depending therefrom, with a hole therethrough.

12. The bone compression and distraction apparatus in claim 11 wherein the elongated tube extends at least one of perpendicular and oblique to the arm as the arm extends through the assembly slot.

13. The bone compression and distraction apparatus in claim 11, wherein the hole terminates within the elongated tube, thereby defining a blind hole.

14. The bone compression and distraction apparatus in claim 11, wherein the elongated tube is rotatable relative to the arm, allowing for rotation of the arm, and in turn the body while being in use.

15. A bone compression and distraction system comprising: A bone compression and distraction apparatus having: A body having an elongated tubular member defining a cavity with a first end and a second end, wherein an assembly slot extends along the length thereof between the first end and the second end; A worm screw extending through the body within the cavity and spaced apart from the body having a first end, a second end, and a central region: a right hand thread extending from the central region toward the first end; a left hand thread extending from the central region toward the second end; at least one end of the worm screw extending beyond the first end of the body and terminating at a ratchet end; and the worm screw configured to rotate about a longitudinal axis extending therethrough while being precluded from translating within the cavity of the body; A first pin attachment member threaded onto the worm screw on the side having the right hand thread and having an arm extending through the assembly slot in the body with the arm having a pin coupling member; and A second pin attachment member spaced apart from the first pin attachment and threaded onto the worm screw on the side having the left hand thread and having an arm extending through the assembly slot in the body with the arm having a pin coupling member; Whereupon rotation of the worm screw causes the first pin attachment member and the second pin attachment member to move in opposing directions along the assembly slot of the body; and At least two pins, each comprising: a first end and a second end, and, having a pointed sharp tip on the first end, and a blunt end on the second end.

16. The bone compression and distraction system in claim 15, wherein each pin includes a stop to limit movement thereof relative to the pin coupling member.

17. The bone compression and distraction system of claim 15 wherein the arm further includes an elongated tube depending therefrom, including a hole extending therethrough, the system further includes a standard coupling interface comprising a standard pin coupling interface having an outwardly conical portion and a cylindrical portion extending therefrom between the first end and the second end of each of the at least two pins, and an arm coupling interface associated with the elongated tube wherein the elongated tube includes a cylindrical bore and in inwardly concave bore extending therefrom, whereupon insertion of the pin into the elongated tube directs the outwardly conical portion of the pin member into contact with the inwardly conical bore to limit further inward movement of the respective pin relative to the elongated tube, and wherein the cylindrical portion of the pin coupling interface is in close association with the cylindrical bore of the arm coupling interface to provide stability between the respective pin and the elongated tube.

18. A bone compression and/or distraction apparatus comprising:

an elongated body;

a worm screw supported for rotation by said elongated body, said worm screw including respective right-hand and left-hand thread forms disposed therealong;

first and second pin attachment members extending laterally from said worm screw and independently slideably disposed with respect to said elongated body, said first pin attachment member operatively engaging said right-hand thread, said second pin attachment member operatively engaging said left-hand thread, said worm screw including an input region adapted to receive rotary inputs from an operator such that rotation of said worm screw in one direction causes linear translation of said first and second pin attachment members toward or away from one another.

19. The bone compression and distraction apparatus of claim 18 wherein said receiving region of said worm screw includes a ratchet mechanism.

20. The bone compression and distraction apparatus of claim 18 wherein said right-hand and left-hand thread forms have substantially equal pitch and thereby effect substantially equal rates of travel of said first and second pin attachment members relative to said elongated body in response to rotation of said worm screw.

21. The bone compression and distraction apparatus of claim 18 further including a bone anchoring pin disposed in each of said first and second pin attachment members.

* * * * *